US00PP12097P2

(12) United States Plant Patent
Zaiger et al.

(10) Patent No.: US PP12,097 P2
(45) Date of Patent: Sep. 18, 2001

(54) INTERSPECIFIC TREE NAMED 'FLAVOR GRENADE'

(76) Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/487,541

(22) Filed: Jan. 19, 2000

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Annette H. Para

(57) ABSTRACT

Our new and distinct variety of interspecific tree [( (*Prunus salicina*×(*Prunus salicina*×*Prunus armeniaca*)×(*Prunus salicina*×*Prunus armeniaca*))]×[(*Prunus salicina*×(*Prunus salicina*×*Prunus armeniaca*)] has the following unique combination of outstanding features that are desirable in a new variety; the features of the tree and its fruit are characterized with the tree budded on 'Nemaguard' Rootstock (non-patented), grown on Hanford sandy loam soil with Storie Index rating 95, in USDA Hardiness Zone 9, near Modesto, Calif., and with standard commercial cultural fruit growing practices, such as, pruning, thinning spraying, irrigation and fertilization:

1. Fruit with very firm, crisp flesh with excellent eating quality.
2. A distinctive blend between plum and apricot with excellent flavor.
3. Moderately juicy, which enhances flavor and eating quality.
4. Fruit with high soluble solids, average Brix 22°.
5. Fruit maintaining firmness on the tree for approximately 21 days after maturity (shipping ripe).
6. Precocious fruit production, usually sets fruit in the second year after planting.
7. Fruit with good handling, shipping quality and shelf life.

1 Drawing Sheet

BACKGROUND OF THE VARIETY

In the field of plant genetics, we conduct an exclusive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plum and interspecific trees, which are known to us, and mentioned herein, 'Mariposa' Plum (U.S. Plant Pat. No. 111), 'Red Beaut' Plum (U.S. Plant Pat. No. 2,539) and the Interspecific tree 'Flavor Queen' (U.S. Plant Pat. No. 7,420).

ORIGIN OF THE VARIETY

The present new variety of interspecific tree [((Plum×(PlumCot)×(PlumCot))]×[(Plum×PlumCot)] was developed by us in our experimental orchard located near Modesto, Calif., as a first generation cross between a selected seedling [field identification number 7HC244 (non-patented)] and 'Flavor Queen' (U.S. Plant Pat. No. 7,420). The maternal parent (7HC244) was selected for a future parent in our breeding program and originated as a seedling selection from a cross between 'Mariposa' Plum (U.S. Plant Pat. No. 111) with the selected plumcot [4G1180 (non-patented)] crossed with the plumcot seedling [42GA580 (non-patented)], both plumcots originated from open pollinated seed of 'Red Beaut' Plum (U.S. Plant Pat. No. 2,539). A large group of these first generation interspecific seedlings, growing on their own root, were planted and maintained under close and careful observation by us in our experimental orchard located near Modesto, Calif. One such seedling, which is the present variety, exhibited the distinctive desirable fruit characteristics described above was selected in 1992 for asexual propagation and commercialization.

ASEXUAL REPRODUCTION OF THE VARIETY

Asexual reproduction, in 1992, of the new and distinct variety of interspecific tree was by budding to 'Nemaguard' Rootstock (non-patented), as performed by us in our experimental orchard located near Modesto, Calif., and shows that reproductions run true to the original tree and all charactristics of tree and the fruit are established and transmitted through succeeding asexual propagations.

SUMMARY OF THE VARIETY

Our present new and distinct variety of interspecific tree is of large size, vigorous, upright growth and is a regular and productive bearer of medium size, yellow flesh, semi-freestone fruit with excellent flavor and eating quality. The fruit is further characterized by having very firm flesh with good handling and shipping quality, having relatively uniform, medium size fruit throughout the tree and the fruit holding firm on the tree 3 weeks after maturity, the fruit having high soluble solids of 22° Brix and relatively uniform maturity throughout the tree. In comparision to the interspecific tree 'Flavor Queen' (U.S. Plant Pat. No. 7,420), the fruit of the new variety has firmer flesh, higher brix, and is approximately 15 days later in maturity. In comparision to the 'Mariposa' Plum (U.S. Plant Pat. No. 111), the flesh of the present variety is firmer with greater shipping quality, yellow compared to maroon; the skin is yellow, partially overspread with red compared to maroon and the fruit is slightly elongated compared to round. In comparision to the 'Red Beaut' Plum (U.S. Plant Pat. No. 2,5391 ), the new variety has fruit which is larger in size, with firmer yellow flesh and is approximately 60 days later in maturity.

PHOTOGRAPH OF THE VARIETY

The accompanying color photograhic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 8 year old specimens grown on 'Nemaguard' Rootstock (non-patented), near Modesto, Calif., with color terminology (except those in common terms) in accordance with Reinhold Color Atlas by A. Kornerup and J. H. Wanscher.

Tree:

*Size.*—Large. Height of tree reduced by pruning to approximately 12 to 14 feet in height for economical harvesting of fruit.

*Vigor.*—Vigorous. Tree growth of 5 to 7 feet the first growing season. Tree is pruned to 3 to 4 feet in height the first dormant season and primary scaffolds are selected.

*Growth.*—Upright. Tree growth is upright in early growth period and width of tree increases as heavy production of fruit tends to pull branches down.

*Productivity.*—Productive. Fruit set is usually two or more times desired for normal crop load and should be thinned and properly spaced to develop desired market fruit size.

*Bearer.*—Regular. Has had heavy fruit production for 5 years.

*Form.*—Usually pruned to vase shape.

*Density.*—Medium dense. Pruning to open center of tree to vase shape improves sunlight and air movement throughout the tree, which improves fruit color and enhances the growth of the fruit bearing wood.

*Hardiness.*—Tree grown in USDA Hardiness Zone 9. Winter chilling requirement is approximately 600 hours below 45° F.

Trunk:

*Size.*—Large. Measured 21 inches in circumference at 12 inches above ground on a 6 year old tree. Varies with soil type and cultural practices.

*Texture.*—Medium shaggy, varies with age of growth.

*Color.*—Mustard brown to tobacco brown (5-E-6) to (5-F-6). Varies with age of tree.

Branches:

*Size.*—Medium. Circumference measured 27 inches above ground varied inches from 6½ inches to 9½ inches. Branches selected with wide angle crotches for primary scaffolds to support heavy crop load.

*Texture.*—Smooth to medium shaggy, varies with age of growth.

*Lenticels.*—Medium number. Medium to large size. Average number of 44 within a 4 square inch section. Average length 5/32 inch. Average width 1/32 inch. Size varies with diameter of branches. Color — light yellow to sunflower yellow (4-C-5) to (4-B-7).

Leaves:

*Size.*—Large. Average length 5¼ inches. Average width 1¾ inches.

*Form.*—Oblanceolate.

*Margin.*—Double serrulate.

*Thickness.*—Medium.

*Surface.*—Upper surface relatively smooth, slightly indented over midrib and pinnate venation, glabrous. Lower surfaces relatively smooth, small ridges created by midrib and pinnate venation, glabrous.

*Petiole.*—Average length ⅝ inch. Average width 1/16 inch. Grooved longitudinally. Color — areas exposed to sunlight vary from pastel pink to light red (11-A-4) to (11-A-7), shaded areas light pink to pastel pink (11-A-2) to (11-A-4).

*Glands.*—Globose and Reinform, varies from one leaf to another. Number varies from 1 to 5. Average number 3. Located on upper portion of petiole and lower portion of leaf blade. Color — Indian yellow to grayish orange (5-B-5) to (6-B-5). Color varies due to sticky secretion collecting dust and impurities from the air during cultural practices.

*Color.*—Upper surface — green to dark green (27-F-6) to (27-F-8). Lower surface — Dull green to bracken green (29-E-5) to (29-E-7).

Flower buds:

*Size.*—Average length 5/16 inch. Average diameter 11/64 inch. Three days before bloom.

*Form.*—Plump, conical.

*Hardiness.*—Hardy in all stone fruit growing areas of california.

*Shape.*—Becomes elongated before opening.

*Pubescence.*—Wanting.

*Color.*—White (1-A-1).

*Pedicel.*—Size — medium. Average length 29/64. Average width 3/64. Color — greenish white to pale green (29-A-2) to (29-A-3).

*Number of buds per spur.*—Usually 4, varies from 3 to 6.

Flowers:

*Size.*—Large. Average height 29/64 inch. Average diameter 31/32 inch.

*Petals.*—Number — five, alternately positioned with sepals. Shape — obovate, narrows at point of attachment. Surface — relatively smooth, edges cupped inwardly toward stamens and pistil. Surface edges vary from smooth to scalloped. Size — average length 25/64 inch. Average width 19/64 inch. Color — white (1-A-1).

*Sepals.*—Number — five, alternately arranged to petals. Size — medium. Average length 9/64 inch. Average width 3/32 inch. Shape — triangular, apex rounded. Color — lower surface olive gray to moss green (1-D-7) to (1-E-7). Upper surface yellowish green to grayish green (29-A-6) to (29-B-6). Both surfaces are glabrous.

*Stamens.*—Number per flower varies from 28 to 34. Average number 30. Average length 23/64 inch. Filament color white (1-A-1). Anther color — yellow to butercup yellow (3-A-7) to (4-A-7).

*Pistil.*—Number — usually 1, varies from 1 to 2. Average length 25/64 inch. Color — yellowish white to pale yellow (2-A-2) to (2-A-3), fades to nearly white as flower matures. Pubescence — wanting. Stigma slightly above anthers.

*Aroma.*—Very slight.

*Pollen.*—Present. Self sterile, pollenizer necessary. Some of the factors affecting blooming dates that must be considered when selecting a pollenizer for specific areas. Winter chilling hours, number of heat units to excite bud initiation, type of rootstock, soil type, cultural practices and climatic conditions. Color — pastel yellow to yellow (3-A-4) to (3-A-6).

*Blooming period.*—Date of First Bloom Feb. 20, 1998. Date of Last Bloom Feb. 27, 1998. Varies slightly with climatic conditions.

*Color.*—White (1-A-1).

*Peduncle.*—Average length ½ inch. Average width 3/64 inch. Color — greenish white to pale green (29-A-2) to (30-A-2).

*Number of flowers per flower bud.*—Usually 2, varies from 1 to 4.

Fruit:

*Maturity when described.*—Firm ripe (shipping ripe).

*Date of first picking.*—Aug. 4, 1998.

*Date of last picking.*—Aug. 12, 1998. Varies slightly with climatic conditions.

*Size.*—Average diameter axially 2½ inches. Average transversely in suture plane 2⅛ inches. Average weight 120 grams. Average weight varies slightly with number of fruit per tree, soil type, climatic conditions and cultural practices.

*Form.*—Slightly elongated in suture plane.

*Suture.*—Shallow, extends from base to apex.

*Ventral surface.*—Nearly rounded.

*Apex.*—Usually rounded, some fruit slightly retuse.

*Base.*—Retuse.

*Cavity.*—Nearly rounded, slightly elongated in suture plane. Average depth ¼ inch. Average breadth ⅜ inch.

Skin:

*Thickness.*—Medium, tenacious to the flesh.

*Surface.*—Very slightly rippled.

*Bloom.*—Moderate amount.

*Tendency to crack.*—None.

*Color.*—Olive yellow to yellow ground color (3-C-8) to (4-B-8). Partially overspread with currant red to orient red (10-B-8) to (10-C-8), with the degree of red color in direct relationship to fruit exposure to sunlight.

Stem:

*Size.*—Average length ¾ inch. Average diameter 3/32 inch.

*Color.*—Light brown to oak brown (5-C-6) to (5-D-6).

Flesh:

*Ripens.*—Evenly.

*Texture.*—Very firm, crisp.

*Fibers.*—Few, small, tender.

*Aroma.*—Very slight.

*Amydgalin.*—Undetected.

*Eating quality.*—Excellent.

*Flavor.*—Excellent, sweet, good balance between sugar and acid.

*Juice.*—Moderate amount, sweet, enhances flavor, lingering after taste.

*Brix.*—Average 22°. Varies slightly with weather conditions during fruit maturity and number of fruit on tree.

*Color.*—Pale orange to melon yellow (5-A-3) to (5-A-6l ). Lightest color of flesh near pit cavity.

*Pit cavity.*—Grayish orange to brownish orange (6-B-6) to (6-C-6).

Stone:

*Type.*—Semi-freestone, only slight adherence to flesh.

*Size.*—Medium. Average length 1 inch. Average width ⅝ inch. Average thickness ⅜ inch.

*Form.*—Obovate.

*Base.*—Varies from straight to slightly retuse at stem attachment.

*Apex.*—Acuminate, short, small.

*Surface.*—Very lightly pitted throughout, two long shallow furrows, one on each side of suture.

*Side.*—Unequal, one side slightly larger.

*Ridges.*—Small and narrow, one on each side of suture and usually two or three extending from base toward apex, approximately ⅓ the length of the stone.

*Tendency to split.*—None.

*Color.*—Light tan to light brown (5-B-4) to (5-C-7).

Kernel:

*Form.*—Oval.

*Taste.*—Bitter.

*Viable.*—Yes.

*Size.*—Average length 9/16 inch, average width 23/64 inch.

*Skin color.*—Grayish orange to golden yellow (5-B-5) to (5-B-7), when dry.

Use: Dessert. Market, local and long distance.

Keeping quality: Good. Fruit stored for 3 weeks at 38° to 42° F., showed no internal browning or wooliness of flesh.

Shipping quality: Good. Picking and packing of fruit gave minimal bruising or scarring of flesh or skin.

Plant disease/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of interspecific tree, substantially as illustrated and described, characterized by its large size, vigorous upright growth and a productive and regular bearer of medium size, very firm, yellow flesh, semi-freestone fruit with excellent flavor and eating quality; the fruit is further characterized by holding firm on the tree for 3 weeks after maturity (shipping ripe), having a high degree of soluble solids (average 22° Brix) and, in comparision to the interspecific tree 'Flavor Queen' (U.S. Plant Pat. No. 7,420), the new variety has firmer flesh, higher Brix, and is approximately 15 days later in maturity.

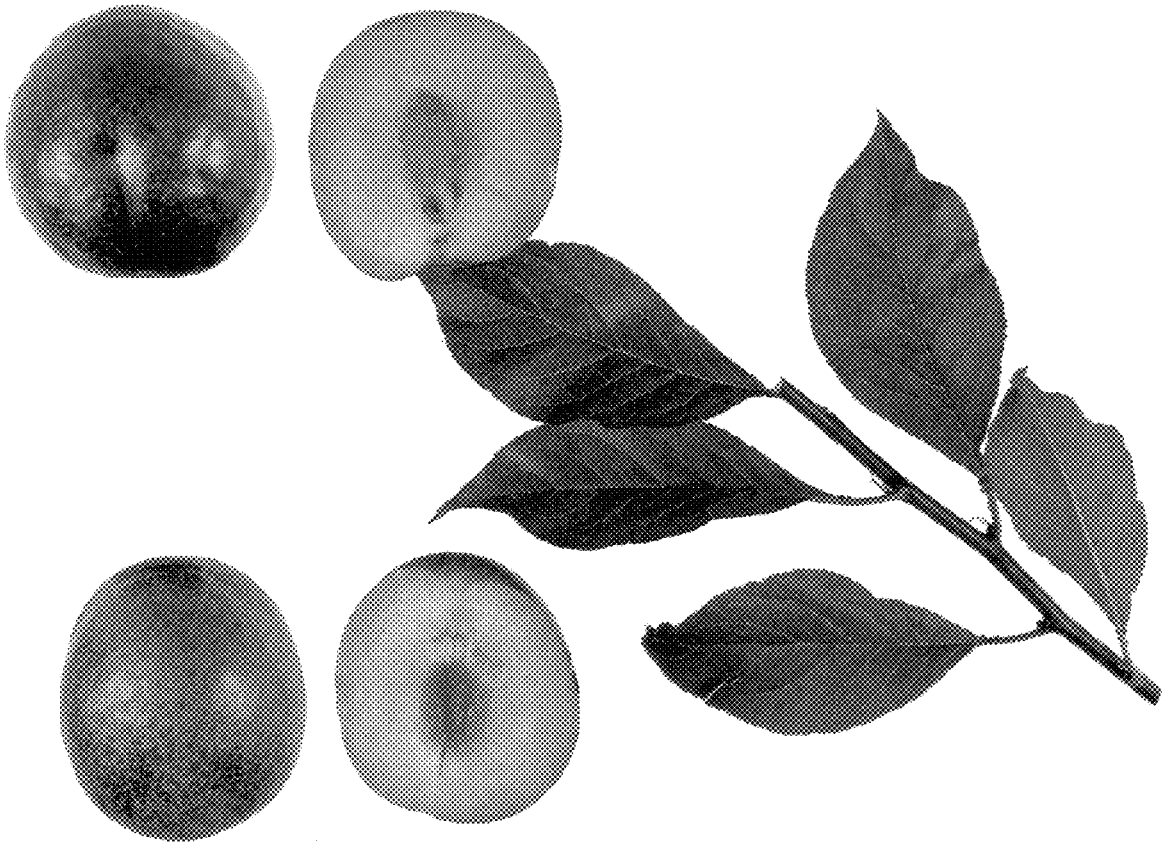

* * * * *